US006758812B2

(12) United States Patent
Lang

(10) Patent No.: US 6,758,812 B2
(45) Date of Patent: Jul. 6, 2004

(54) EMERGENCY MEDICAL TREATMENT SYSTEM

(76) Inventor: Brook W. Lang, 40 Lake Bellevue, Suite 100, Bellevue, WA (US) 98005

(*) Notice: Subject to any disclaimer, the term of this patent is extended or adjusted under 35 U.S.C. 154(b) by 7 days.

(21) Appl. No.: 10/080,447

(22) Filed: Feb. 22, 2002

(65) Prior Publication Data

US 2002/0118112 A1 Aug. 29, 2002

Related U.S. Application Data

(60) Provisional application No. 60/271,034, filed on Feb. 23, 2001.

(51) Int. Cl.[7] .................. A61B 5/00

(52) U.S. Cl. .................. 600/300; 128/903

(58) Field of Search .................. 600/300–301, 600/529, 536; 128/903, 904, 905, 920, 921; 705/2–4; 340/573.1; 455/404; 342/457

(56) References Cited

U.S. PATENT DOCUMENTS

| | | | | |
|---|---|---|---|---|
| 5,997,476 A | * 12/1999 | Brown | ........ | 600/300 |
| 6,468,222 B1 | * 10/2002 | Mault et al. | ........ | 600/531 |
| 6,478,736 B1 | * 11/2002 | Mault | ........ | 600/300 |

OTHER PUBLICATIONS

John Lortz and Susan Leavitt, "What is Bluetooth? We Explain The Newest Short–Range Connectivity Technology" 2002, Sandhill Publishing, Smart Computing Learning Series Wireless Computing, pp. 72–74.*

Ron White, "How Computers Work" Sep. 2001, Que Corporation, 6th Edition, pp. 258–259, and 327.*

* cited by examiner

*Primary Examiner*—Mary Beth Jones
*Assistant Examiner*—Michael Astorino
(74) *Attorney, Agent, or Firm*—Dean A. Craine

(57) ABSTRACT

An emergency medical treatment system that uses medical information recorded in a user file by a central computer connected to a wide area network. The system is designed to be used with a recording and monitoring health and physical fitness system that automatically sends the parameter information from a sensor worn by a subscriber to a central computer. The wireless communication unit is able to connect to a wireless communication network which, in turn, connects to a wide area network. A central computer is connected to a wide area network that is able to continuously download the physiological parameter information from the wireless communication unit via the wireless communication network. The central computer uses a health information recording software program to create a continuously updated subscriber's medical database containing current and historical medical information. The subscriber and authorized medical personnel are able to log onto the central computer to review the medical information on the subscriber's medical database file.

4 Claims, 2 Drawing Sheets

EMERGENCY MEDICAL TREATMENT SYSTEM

This is a utility patent application based on a provisional patent application (Serial No. 60/271,034) filed on Feb. 23, 2001.

BACKGROUND OF THE INVENTION

1. Field of the Invention

This invention relates to medical treatment systems, and, more particularly, to such systems designed for providing emergency medical care.

2. Description of the Related Art

When an individual becomes incapacitated or unconscious during a medical emergency, the medical personnel who arrive to give medical treatment are often unaware of the individual's medical condition or medical history. In some instances, a medical identification card carried by the individual or someone who knows the individual may be present to provide some useful information to the medical personnel. Unfortunately, these cards and individuals may not always be available or may provide insufficient information.

Hospitals and medical clinics have been using local area networks to record and review medical files for their patients. Recently, wide area networks have been also developed which enable individuals to record their exercise activities, eating habits, and medical information on a central server connected to the network. Such systems are especially useful because users are able to upload and download information from the network from any location in the region capable of being connected to a wired or wireless telephone network. Such systems have been disclosed in U.S. patent applications Ser. Nos. 09/619,132, 09/645,461, and 60/248,982.

What is needed is ann emergency medical treatment system designed to allow authorized healthcare personnel to quickly review a patient's medical information stored on the wide area network from any location in a region.

SUMMARY OF THE INVENTION

It is an object of the present invention to provide an improved emergency medical treatment system.

It is an object of the present invention to provide such a system that provides medical information for users who subscribe to a single, comprehensive medical information storage system that enables authorized medical personnel located over a large region to quickly and easily download the user's medical information.

It is a further object of the present invention to provide such a system that uses currently available technology thereby expediting the system's implementation.

These and other objects are met by an emergency medical treatment system disclosed herein designed to allow a subscriber to store health parameter information that emergency medical personnel can quickly access.

The system includes a wireless communication unit that receives health parameter information and then stores it in memory or transmits it to a central computer connected to a wide area network. In one embodiment, the wireless communication unit is coupled to at least one physiological parameter measurement means attached to the subscriber that accurately measures a desired physiological parameter of a subscriber, such as heart rate, blood pressure, respiratory rate, body temperature, etc. In the preferred embodiment, the wireless communication unit is a data-communication enabled wireless telephone capable of connecting to a wireless communication network. Each wireless communication unit may also include or may be coupled to an optional physical location means used to establish the subscriber's exact physical location at any time in the region when the health parameter information is received by the unit. The wireless communication network is connected to a wide area computer network so that the wireless communication unit is able to connect to a central computer connected to the wide area computer network. The physiological parameter measurement means may be worn or carried by the subscriber during selected periods or activities during the day or it may be worn or carried continuously throughout the entire day, so that the subscriber's physiological parameter information may be immediately or intermittently processed and transmitted to the central computer through the wide area computer network. When the central computer receives the time, date, location, and physiological parameter information, it is stored in the subscriber's medical database file. During use, the subscriber's medical database file is constantly updated, thereby creating both current and historical medical information. The data in the subscriber's medical database file can be downloaded from the central computer by the subscriber or other authorized individuals capable of connecting to the wide area network. Not only can authorized individuals evaluate the subscriber's current and historical medical information if the subscriber is incapacitated during a medical emergency, but also enables them to identify events or situations that occurred simultaneously with the changes to the subscriber's physiological parameter information.

Loaded into the memory of the central computer or in a second computer connected to or in communication with the central computer is a health information recording software program that is used to set up the subscriber's medical database file and the permission file, and collect data from the physiological parameter measurement means, and to process requests for data from the subscriber's medical database file. During use, the subscriber controls and monitors which individuals are downloading information from the subscriber's medical database file. During use, the subscriber's authorization file creates a logbook and calendar for authorized individuals who download information. When initially setting up the program, the subscriber may give his or her physician or local area hospital personnel "blanket" permission to download the information from the user's medical database file.

In another embodiment, the health information recording software and the medical database and authorized user files are stored in memory on the wireless communication unit.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

DESCRIPTION OF THE PREFERRED EMBODIMENT (S)

Figure 1:
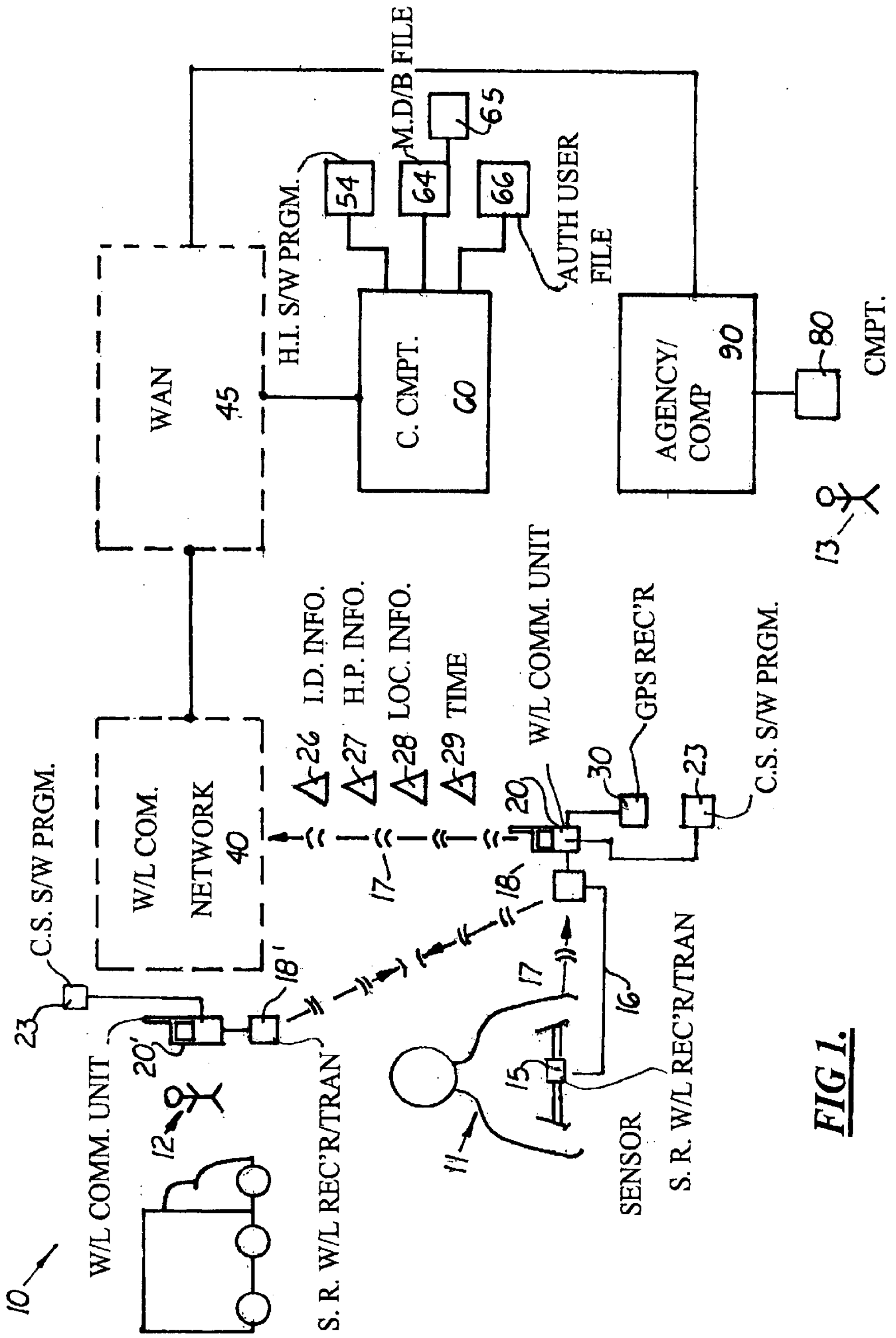
FIG. 1 is an illustration showing the emergency medical treatment system disclosed herein.

In FIG. 1, an emergency medical treatment system 10 is shown, designed to enable emergency medical personnel to obtain medical information on subscribers 11 to the system 10. The system 10 enables emergency medical personnel 12 and other authorized users 13 to quickly download medical information from the subscriber's medical database file 64 anywhere in a large region. In the first embodiment, the system 10 includes a central computer 60 connected to a wide area network 45. Medical information is stored in a subscriber's medical database file 64 loaded into the memory of the central computer 60 which can be reviewed by the subscriber 11, by emergency medical personnel 12, or by other authorized users 13 at any time.

The system 10 is designed to be used independently or with the exercise monitor system disclosed in the U.S. patent application entitled, "Comprehensive Personal Exercise Monitoring System" (Ser. No. 60/248,982) and incorporated herein, which includes a physiological parameter measurement sensor 15 worn or attached to the subscriber 11 and coupled to a wireless communication unit 20 worn or carried by the subscriber 11 or located nearby. Each wireless communication unit 20 is capable of transmitting digital data over a wireless communication network 40. During use, the wireless communication unit 20 transmits the health and physical fitness parameter information, hereinafter referred to as health parameter information 27 and location information 28, over the wireless communication network 40 to a wide area network 45 and eventually to a central computer 60 connected thereto. The central computer 60 collects the uploaded health parameter information 27 and location information 28 from the wireless communication unit 20. The subscriber's health parameter information 27 is then stored in a subscriber medical database file 64 created by a health information recording software program 54 loaded into the memory of the central computer 60.

Each wireless communication unit 20 is designed to continuously, or intermittently, upload the health parameter information 27 from one or more sensors 15 worn by the subscriber 11 or other subscribers (not shown) located in the area covered by the wireless communication network 40. The central computer 60 receives the information 27, 28 so that the subscriber medical database file 64 is constantly and immediately updated. In the preferred embodiment, the wireless communication unit 20 includes an optional physical location-detecting means that determines the subscriber's specific physical location at the time the health parameter information 27 is collected, or at the time the wireless communication unit 20 is connected to the wide area network 45. In the embodiment shown, the physical location means is a global positioning system (GPS) receiver 30. That is able to immediately establish the monitoring device's global position, (i.e. latitude, longitude, elevation), heading, and velocity. It should be understood, however, that other types of physical location means may be used, such as cellular telephone network cell site triangulation.

It should be understood that the wireless communication unit 20 may be a built-in component in the sensor 15 or it may be a separate component coupled to the sensor 15 via a wired communication link 16 as shown in FIG. 1. It should also be understood that the wired communication link 16 may be replaced with a short-range wireless connection link 17. One type of short-range wireless connection link 17 designed to a suitable receiver/transmitter 18 available under the wireless connection system sold under the trademark BLUETOOTH from Telefonaktiebolaget LM Ericsson, which is now incorporated herein. Such devices have a maximum range of about 10 meters and operate in the 2.4 to 2.5 gigahertz band.

The GPS is a location system based on a constellation of twenty-four satellites orbiting the Earth at altitudes of approximately 11,000 miles. The GPS satellites provide accurate positioning information twenty-four hours per day, anywhere in the world. The GPS uses a receiver that stores orbit information for all GPS satellites. During use, the receiver 30 determines the time and the positions of the overhead satellites and then calculates the amount of time it takes a GPS radio signal to travel from the satellites to the GPS receiver 30. By measuring the amount of time it takes for a radio signal to travel from the satellites, the exact location of the GPS receiver 30 can be determined. GPS receivers 30 are available from Corvallis Microtechnology, Inc., in Corvallis, Oreg. It should be understood however, that other means for automatically determining the user's physical location could be used.

In the preferred embodiment, the wireless communication unit 20 includes a GPS receiver 30 that uses 3-D coordinate receivers that require a minimum of four visible satellites. It should be understood, however, that the system 10 could be used with 2-D coordinate receivers, which require a minimum of three satellites. The 3-D coordinate receivers are preferred, since they will continue to provide 2-D coordinate information when trees, mountains, buildings, etc. obstruct their views.

When the GPS receiver 30 is turned on, it immediately provides a "fix" position. As it continues to operate, it records "waypoints" at pre-determined intervals (i.e. 1–5 seconds). A client-side software program 23, discussed further below, is designed to receive the "fix" and "waypoints" coordinates and transmit them to the central computer 60 as part of the location information 28.

Loaded into the memory of each wireless communication unit 20 is a client-side software program 23 that enables the wireless communication unit 20 to communicate with a health information recording software program 54 loaded in the central computer 60. During use, the client-side software program 23 collects the health parameter information 27, the time 28, and the location information 29 from the wireless communication unit 20 and uploads it to the central computer 60. Also, when the subscriber 11 initially logs into the system 10, the client-side software program 23 automatically transmits the subscriber's identification information 26, such as the user's name and password, so that the subscriber 11 may access his or her medical database file 64.

As discussed above, the central computer 60 is able to communicate via the wide area network 45 with a plurality of wireless communication units 20 all connected to the network 45. It should be understood that the central computer 60 may be one server or a group of servers all connected to the wide area network 45. As discussed above, loaded into the memory of the central computer 60 is the health information recording software program 54 capable of uploading and processing the data 26–29 from the client-side software program 23. The health information recording software program 54 is also used to handle requests for data from a specific medical database file 64 and download requested data to the subscriber 11 or authorized user 12, 13.

In order to use the system 10, the wireless communication unit's network address must be known to the central computer 60 so that information 26–29 may be downloaded thereto. If the central computer 60 is also the authorized subscriber's network service provider to the wide area network 45 and a previously established account has been set up on the central computer 60, the numerical or temporary address would be known to the central computer 60 when the subscriber 11 signs onto the central computer 60. If the subscriber 11 does not have a previously established account on the central computer 60, then the client-side software program 23 must be used to collect and transfer the user's account information 26 to the central computer 60 each time the subscriber 11 logs onto the central computer 60.

During use, the user's personal information is entered into the client-side software program 23. When initial contact is made with the central computer 60, the personal information is automatically downloaded to the central computer 60. The client-side software program 23 may be a proprietary software program, or may be included as an add-on to an existing INTERNET browser software program. After the account information has been confirmed or set up on the central computer 60, the user 11 may begin to download and/or upload information from the central computer 60.

Currently, many companies manufacture and sell wireless medical data communication devices with built-in sensors designed to measure a health parameter of a subscriber that can be used in the system 10. Such devices are available from Data Critical Corporation of Seattle, Wash., are sold under the trademarks STATVIEW, POCKETCHART, and WEBCHART, and are incorporated herein.

The system 10 allows emergency medical personnel 12 or other authorized individuals 13, 13' to download the health parameter information 27 from the subscriber's medical database file 64. In one embodiment shown in FIG. 2, the wireless communication unit 20 includes a label or button 80 informing the user, such as an emergency medical personnel 12 of the wireless communication unit 20', that the owner of the first wireless communication unit 20 is a subscriber to the system 10. During an emergency, the emergency medical personnel 12 is able to push a direct access button 70 to immediately obtain data from the subscriber's medical database file 64. The second wireless communication unit 20' has copy of the client-side software program 23 loaded into its memory that enables it to communicate with the first wireless communication unit 20 or the central computer 60.

An important benefit of the above-described system 10 is that authorized personnel 13 located in a building may use a landline telephone to connect to the central computer 60 to obtain data from the file 64. In order to do so, however, both the emergency medical personnel 12 and authorized users 13 must be in the authorized user file 66 created on the central computer 60.

In another embodiment of the system, copies of the health parameter information 27, and authorized file 66 is stored in memory in the communication unit 20. During an emergency, emergency medical personnel 12 may use a second wireless communication unit, denoted 20' to communicate directly with the subscriber's communication unit 20. Both units, 20, 20' include a short range wireless receiver/transmitter 18, 18' respectively that enable the two units 20, 20' to communicate. The emergency medical personnel 12 point his or her communication unit 20' at the subscriber's communication unit 20 and immediately begins to download data from the medical database file 64 located on the unit 20.

Figure 2:
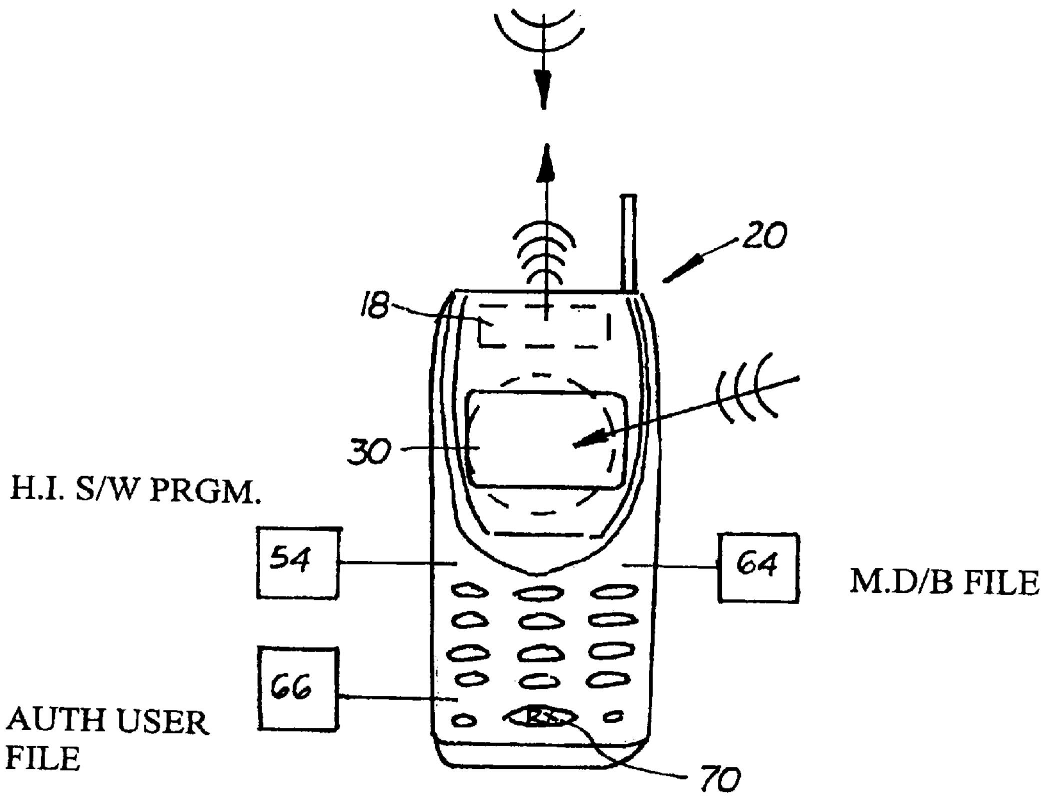
FIG. 2 is a plan view of a wireless communication unit with an optional GPS receiver, a short range wireless receiver/transmitter and a direct access button.

FIG. 2 is a plan view of a wireless communication unit 20 with a built-in short-range wireless receiver/transmitter 18, an optional GPS receiver 30 and medical database file 64, and an optional authorized user file 66.

The following example illustrates how the system may be used:

Monitoring and Download Information

The system 10 is designed to enable authorized subscribers to continuously or batch upload health parameter information 27 to a central computer 60 located in a region. By enabling this information 27 to be continuously or batch uploaded into the central computer 60, the impact of the subscriber's exercise, non-exercise, social, and environmental factors and activities may be accessed and evaluated.

The subscriber 11 first selects a sensor 15, such as a heart-monitoring device, hardwired to a wireless communication unit 20 that includes a built in wireless modem 25 and a GPS receiver 30. The wireless communication unit 20 may be a handheld, personal digital assistant connected to a wireless modem or a web-enabled cellular telephone. A suitable client-side software program 23 is loaded into the wireless communication unit 20 so that it may connect to the central computer 60. The subscriber 11 may turn on the sensor 15 and wireless communication unit 20 and immediately begin downloading the health parameter information 27 to the central computer 60.

An authorized user 13 uses his or her wireless communication unit 20 or another remote computer 80 to automatically or selectively request the subscriber's medical data 65 from the central computer 60. The central computer 60 processes the request by first verifying the user's account information in the subscriber database file 64. The desired information is then downloaded from the central computer 60 to the wireless communication unit 20 or the remote computer 80. The downloaded information from the central computer 60 may be displayed on a graphic interface, transmitted audibly through speakers, or downloaded to a printer. Also, the requested data 65 may be automatically delivered at designated time intervals, or upon request. The important aspect of the system 10 is that the requested data 65 is constantly updated by the subscriber 11 of the system 10.

In compliance with the statute, the invention, described herein, has been described in language more or less specific as to structural features. It should be understood, however, the invention is not limited to the specific features shown, since the means and construction shown comprise only some of the preferred embodiments for putting the invention into effect. The invention is, therefore, claimed in any of its forms or modifications within the legitimate and valid scope of the amended claims, appropriately interpreted in accordance with the doctrine of equivalents.

I claim:

1. An emergency medical treatment system, comprising:

a. a central computer;

b. a health information recording software program loaded into said central computer, said health information recording software program used to collect and process physiological parameter information delivered thereto;

c. wide area network connected to said central computer;

d. a wireless communication network connected to said wide area network;

e. a first wireless telephone to communicate with said wireless communication network;

f. at least one physiological parameter monitoring means worn by an individual and used to measure a desired physiological parameter, said monitoring means coupled to said first wireless telephone to transmit physiological information for said individual to said central computer connected to said wide area network;

g. a first client-side software program loaded into said first wireless telephone enabling said first wireless communication means telephone to communicate with said central computer;

g. a first short-range receiver/transmitter connected to said first wireless telephone; and, h. a second wireless telephone with a second short range receiver/transmitter used to communicate with said first short-range receiver/transmitter connected to said first wireless telephone, said second short range receiver/transmitter being used during an emergency medical situation to retrieve said physiological information delivered to said first wireless telephone by said physiological parameter monitoring means for providing emergency medical treatment to said individual.

2. The emergency medical treatment system, as recited in claim 1, wherein said physiological parameter monitoring means is coupled to said first wireless telephone by a short-range wireless communication link.

3. The emergency medical treatment system, as recited in claim 1, further including means located on said first wireless telephone for visually indicating whether said individual is a subscriber to said system.

4. The emergency medical treatment system, as recited in claim 1, further including a second client-side software program loaded into said second wireless telephone enabling said second wireless telephone to communicate with said first client-side software program on said central computer to retrieve health parameter information for said individual from said central computer during an emergency medical treatment situation.

* * * * *